(12) United States Patent
Shecterle

(10) Patent No.: US 7,638,665 B2
(45) Date of Patent: *Dec. 29, 2009

(54) ISOMERIZATION OF BENZENE-CONTAINING FEEDSTOCKS

(75) Inventor: David J. Shecterle, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/418,152

(22) Filed: Apr. 3, 2009

(65) Prior Publication Data

US 2009/0187054 A1  Jul. 23, 2009

Related U.S. Application Data

(63) Continuation of application No. 11/750,521, filed on May 18, 2007, now Pat. No. 7,534,925.

(51) Int. Cl.
*C07C 5/22* (2006.01)
*C07C 5/32* (2006.01)

(52) U.S. Cl. .................... 585/315; 585/311; 208/57; 208/63

(58) Field of Classification Search ........... 585/315, 585/310; 208/57, 63
See application file for complete search history.

(56) References Cited

U.S. PATENT DOCUMENTS

| | | |
|---|---|---|
| 3,761,392 A | 9/1973 | Pollock |
| 4,181,599 A | 1/1980 | Miller et al. |
| 4,457,832 A | 7/1984 | Robinson |
| 4,834,866 A | 5/1989 | Schmidt |
| 5,003,118 A | 3/1991 | Low et al. |
| 5,360,534 A | 11/1994 | Rice et al. |
| 5,453,552 A | 9/1995 | Rice et al. |
| 5,463,155 A | 10/1995 | Galperin et al. |
| 5,663,466 A | 9/1997 | Rice et al. |
| 5,763,713 A | 6/1998 | Blommel et al. |
| 5,888,922 A | 3/1999 | Galperin |
| 5,905,181 A | 5/1999 | Galperin |
| 2008/0287724 A1 | 11/2008 | Shecterle |

OTHER PUBLICATIONS

U.S. Appl. No. 11/750,525, filed May 18, 2007, David J. Shecterle, USPTO Office Action mailed Jul. 10, 2008.
U.S. Appl. No. 11/750,525, filed May 18, 2007, David J. Shecterle, Applicant's Amendment After Non-Final Rejection in the USPTO dated Dec. 18, 2008.
U.S. Appl. No. 11/750,525, filed May 18, 2007, David J. Shecterle, Telephone Interview dated Jan. 15, 2009.
U.S. Appl. No. 11/750,525, filed May 18, 2007, David J. Shecterle, USPTO Notice of Allowance mailed Jan. 27, 2009.

*Primary Examiner*—Thuan Dinh Dang
(74) *Attorney, Agent, or Firm*—Maryann Maas

(57) ABSTRACT

The benzene content in a gasoline pool is reduced by a process that hydrogenates a benzene-containing isomerization zone feedstream. The additional cyclic hydrocarbons produced by the saturation of benzene can be processed in the isomerization zone for ring opening to increase the available paraffinic feedstock or the isomerization zone can be operated to pass the cyclic hydrocarbons through to a product recovery section. The isomerization zone feedstream is treated to remove contaminants and dried before entering the hydrogenation zone.

16 Claims, 1 Drawing Sheet

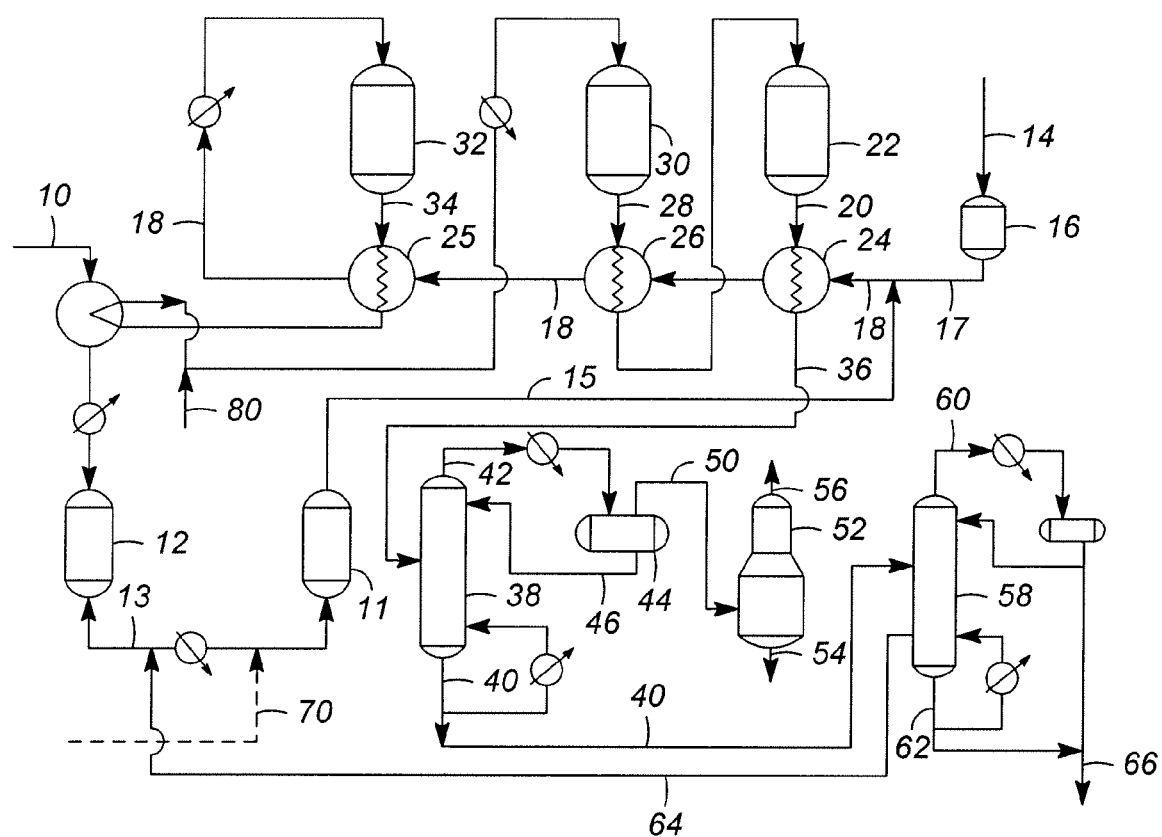

ISOMERIZATION OF BENZENE-CONTAINING FEEDSTOCKS

CROSS-REFERENCE TO RELATED APPLICATION

This application is a Continuation of copending application Ser. No. 11/750,521 filed May 18, 2007, the contents of which are hereby incorporated by reference in its entirety.

FIELD OF THE INVENTION

This invention relates generally to the isomerization of hydrocarbons. This invention relates more specifically to the processing of benzene-containing hydrocarbon feeds and the isomerization of light paraffins.

BACKGROUND OF THE INVENTION

High octane gasoline is required for modern gasoline engines. Benzene has a high octane number value and has been previously blended into gasoline. However, as benzene is phased out of gasoline for environmental reasons, it has become increasingly necessary to rearrange the structure of the hydrocarbons used in gasoline blending in order to achieve high octane ratings. Catalytic reforming and catalytic isomerization are two widely used processes for this upgrading.

A gasoline blending pool is usually derived from naphtha feedstocks and includes $C_4$ and heavier hydrocarbons having boiling points of less than 205° C. (395° F.) at atmospheric pressure. This range of hydrocarbon includes $C_4$-$C_9$ paraffins, cycloparaffins and aromatics. Of particular interest have been the $C_5$ and $C_6$ normal paraffins which have relatively low octane numbers. The $C_4$-$C_6$ hydrocarbons have the greatest susceptibility of octane improvement by lead addition and were formerly upgraded in this manner. Octane improvement can also be obtained by catalytically isomerizing the paraffinic hydrocarbons to rearrange the structure of the paraffinic hydrocarbons into branch-chained paraffins or reforming to convert the $C_6$ and heavier hydrocarbons to aromatic compounds. Normal $C_5$ hydrocarbons are not readily converted into aromatics, therefore, the common practice has been to isomerize these lighter hydrocarbons into corresponding branch-chained isoparaffins. Although the non-cyclic $C_6$ and heavier hydrocarbons can be upgraded into aromatics through dehydrocyclization, the conversion of $C_6$'s to aromatics creates higher density species and increases gas yields with both effects leading to a reduction in liquid volume yields. Therefore, it is preferable to charge the non-cyclic $C_6$ paraffins to an isomerization unit to obtain $C_6$ isoparaffin hydrocarbons. Consequently, octane upgrading commonly uses isomerization to convert normal $C_6$ and lighter boiling hydrocarbons and reforming to convert $C_6$ cycloparaffins and higher boiling hydrocarbons.

In the reforming processing, $C_6$ cycloparaffins and other higher boiling cyclic hydrocarbons are converted to benzene and benzene derivatives. Since benzene and these derivatives have a relatively high octane value, the aromatization of these naphthenic hydrocarbons has been the preferred processing route. However, many countries are contemplating or have enacted legislation to restrict the benzene concentration of motor fuels. Therefore, processes are needed for reducing the benzene content of the gasoline pool while maintaining sufficient conversion to satisfy the octane requirements of modern engines.

Combination processes using isomerization and reforming to convert naphtha range feedstocks are well known. U.S. Pat. No. 4,457,832 uses reforming and isomerization in combination to upgrade a naphtha feedstock by first reforming the feedstock, separating a $C_5$-$C_6$ paraffin fraction from the reformate product, isomerizing the $C_5$-$C_6$ fraction to upgrade the octane number of these components and recovering a $C_5$-$C_6$ isomerate liquid which may be blended with the reformate product. U.S. Pat. Nos. 4,181,599 and 3,761,392 show a combination isomerization-reforming process where a full range naphtha boiling feedstock enters a first distillation zone which splits the feedstock into a lighter fraction that enters an isomerization zone and a heavier fraction that is charged as feed to a reforming zone. In both the '392 and '599 patents, reformate from one or more reforming zones undergoes additional separation and conversion, the separation including possible aromatics recovery, which results in additional $C_5$-$C_6$ hydrocarbons being charged to the isomerization zone.

The benzene contribution from the reformate portion of the gasoline pool can be decreased or eliminated by altering the operation of the reforming section. There are a variety of ways in which the operation of the reforming section may be altered to reduce the reformate benzene concentration. Changing the cut point of the naphtha feed split between the reforming and isomerization zones from 82 to 93° C. (180° to 200° F.) will remove benzene, cyclohexane and methylcyclopentane from the reformer feed. Benzene can alternately also be removed from the reformate product by splitting the reformate into a heavy fraction and a light fraction that contains the majority of the benzene. Practicing either method will put a large quantity of benzene into the feed to the isomerization zone.

The isomerization of paraffins is a reversible reaction which is limited by thermodynamic equilibrium. The basic types of catalyst systems that are used in effecting the reaction are a hydrochloric acid promoted aluminum chloride system and a supported aluminum chloride catalyst. Either catalyst is very reactive and can generate undesirable side reactions such as disproporationation and cracking. These side reactions not only decrease the product yield but can form olefinic fragments that combine with the catalyst and shorten its life. One commonly practiced method of controlling these undesired reactions has been to carry out the reaction in the presence of hydrogen. With the hydrogen that is normally present and the high reactivity of the catalyst, any benzene entering the isomerization zone is quickly hydrogenated. The hydrogenation of benzene in the isomerization zone increases the concentration of napthenic hydrocarbons in the isomerization zone.

It has been discovered that placing a hydrogenation reaction zone in front of an isomerization reaction zone but downstream of the feed driers required for the isomerization catalyst allows savings by reduction of equipment count and cost as well as a reduction in the amount of hydrogen required for the process. Placing the hydrogenation reaction zone downstream of the feed driers, allows the product condensers and receiver that would normally be required downstream of the hydrogenation reactor to be eliminated. Because the receiver has been eliminated, there is no hydrogen venting required. Hydrogen is a valuable commodity to refiners who are in need of ways to reduce hydrogen usage. Furthermore, in the present invention, low pressure feed driers may be used. Driers that are only operated at low pressures are less costly than high pressure driers and the cost of the many valves associated with the driers for the purposes of regenerating the drier sieves is reduced significantly for low pressure driers. Finally, additional utility savings are realized by the elimination of the condensing equipment normally required downstream of the hydrogenation reaction zone.

SUMMARY OF THE INVENTION

This invention is a process for converting a feedstock comprising $C_4$-$C_7$ paraffins and $C_5$-$C_7$ cyclic hydrocarbons including benzene. This invention uses a hydrogenation zone upstream of the isomerization reactors to saturate benzene and simultaneously heat the feed to the isomerization zone. The use of a separate hydrogenation zone also lowers the overall temperature of the isomerization zone feed as the benzene is saturated—lower temperatures minimize undesirable hydrocracking reactions. Also performing the highly exothermic benzene saturation reaction in a lead reactor that has a lower temperature reduces the coking that could occur in the isomerization zone as a result of the higher overall temperatures.

Accordingly in one embodiment, this invention is a process for the isomerization of a $C_4$-$C_6$ paraffinic feedstock that contains at least 1 wt.-% benzene. The process includes the steps of combining the feedstock with a hydrogen-rich gas stream to produce a combined feed. The combined feed is passed to a hydrogenation zone and contacted therein with a hydrogenation catalyst to saturate benzene and heat the feedstream. The saturated feedstream is recovered from the hydrogenation zone and has a benzene concentration of less than 1.5 wt.-%. At least a portion of the saturated feedstream is passed from the hydrogenation zone to an isomerization zone without heating and contacted with an isomerization catalyst at isomerization conditions.

In a yet further embodiment, this invention is a process for the isomerization of $C_5$-$C_6$ paraffinic feedstock that contain at least 1 wt.-% benzene. The process dries the feedstock before combining the feedstock with a dried hydrogen-rich gas to produce a combined feed that is passed at a temperature of from 38 to 232° C. (100 to 450° F.) to an hydrogenation zone and contacted therein with a hydrogenation catalyst. In another embodiment the temperature of the combined feed is 127 to 232° C. (260 to 450° F.) or 149 to 204° C. (300 to 400° F.). To heat the combined feed, the combined feed may be heat exchanged with isomerization and hydrogenation zone effluents. Contact with the hydrogenation catalyst saturates the benzene and the exothermic reaction heats the saturated feedstream (hydrogenation zone effluent) to a temperature of from 149 to 288° C. (200 to 450° F.). In another embodiment the saturated feedstream is heated to 177 to 274° C. (350 to 525° F.) or 204 to 274° C. (400 to 525° F.). The saturated feedstream has a benzene concentration of from about 0.01 to about 5 wt-% or from about 0.1 to about 1.5 wt.-% and is heat exchanged with the combined feed and the feedstock, and possibly cooled, before being passed to an isomerization zone. The saturated feedstream is contacted with an isomerization catalyst in the isomerization zone to isomerize $C_5$-$C_6$ hydrocarbons. An isomerate product essentially free of benzene is recovered from the isomerization zone. Downstream separations may be used to recycle low octane components of the isomerization zone effluent.

Other embodiments, aspects and details of this invention are disclosed in the following detailed description of the invention.

BRIEF DESCRIPTION OF THE DRAWING

The FIGURE shows a schematic flow diagram of one embodiment of the process.

DETAILED DESCRIPTION OF THE INVENTION

A basic arrangement for the processing equipment used in this invention can be readily understood by a review of the flow scheme presented in the FIGURE. The FIGURE does not show all pumps, condensers, reboilers, instruments and other well-known items of processing equipment in order to simplify the drawing. However, the discussion points out several items of traditional processing equipment that may be eliminated and thus provide both a capital cost savings and an operational cost savings.

Looking at the FIGURE, a feedstream comprising at least $C_5$ and $C_6$ paraffins along with at least 1 wt.-% benzene enter the process through line 10 and pass through a sulfur guard bed 12 that removes sulfur from the feedstream. The sulfur-depleted feedstream in line 13 is passed through a low pressure drier 11 to remove water. It is important to note that line 13 is not passed through a reactor, nor is hydrogen added, before being dried in low pressure drier 11. This eliminates the need for product condensers and a receiver on line 13. The elimination of a commonly used condenser provides an operational and equipment cost savings, and the elimination of the receiver additionally eliminates the need for a hydrogen vent. Hydrogen is a valuable component in refineries today, and conservation of hydrogen results in positive value for the refiner. Finally, only a low pressure drier 11 is required. High pressure driers and their associated valves are far more costly than low pressure driers and their associated valves. Thus a cost savings is realized in requiring only a low pressure drier as opposed to a high pressure drier.

Make-up hydrogen enters the process through line 14 and passes through a drier 16 for removal of water and sulfur. The dried feedstream in line 15 and the dried hydrogen from line 17 are combined in line 18 to form a combined feed. The combined feed 18 is heat exchanged in an exchanger 24 against the contents of line 20 which carries the effluent from a second isomerization reactor 22. The contents of line 18 are further heat exchanged in a heat exchanger 26 against the contents of line 28 which carries the effluent from a first isomerization reactor 30. The contents of line 18 are still further heat exchanged in a heat exchanger 25 against the contents of line 34 which carries the effluent from a dehydrogenation reactor 32. The hydrogenation reactor 32 receives the contents of line 18, the combined feed. The hydrogenation reactor saturates benzene present in the combined feed and further heats the combined feed. Line 34 carries a saturated feed from hydrogenation reactor 32 to the first isomerization reactor 30. A chloride-containing compound is injected into the contents of line 34 by a line 80.

A first stage of isomerization takes place in reactor 30. Following the first stage of isomerization, the effluent in line 28 is exchanged in heat exchanger 26 against the combined feed in line 18 as discussed above. Line 28 then carries the partially cooled isomerization effluent from reactor 30 to reactor 22. After further isomerization in reactor 22, an isomerate product is taken by line 20, heat exchanged against the combined feed in line 18 using heat exchanger 24 and then is passed to a fractionation column 38. Fractionation column 38 removes light gases from the isomerate product which are taken overhead by line 42 and withdrawn from the process through the top of a receiver 44 via line 50. Recycle is conducted back to fractionation column 38 via line 46. The stabilized isomerate product is withdrawn from the bottom of fractionation column 38 by line 40. To increase efficiency, stabilized isomerate product in line 40 is conducted to deisohexanizer 58 to separate low octane alkanes, such as normal or single branched isoparaffins and cyclic compounds such as cyclohexane, for recycle to the isomerization zone via line 64. Valuable isomerate product in lines 60 and 62 are combined into final product 66.

Suitable feedstocks for this invention will include $C_4$ plus hydrocarbons up to an end boiling point of about 250° C. (482° F.). The feedstocks that are used in this invention will typically include hydrocarbon fractions rich in $C_4$-$C_6$ normal paraffins. The term "rich" is defined to mean a stream having more than 50% of the mentioned component. In addition, the feedstock will include significant amounts of benzene. The concentration of benzene in the feedstock will at least equal 1.0 wt.-% and will normally be higher. The concentration of benzene may be from 1 to 25 wt.-%, and is expected to usually be in the range of 3 to 15 wt.-% or 5 to 12 wt.-%. The other feed components will usually comprise $C_5$-$C_6$ cyclic and paraffinic hydrocarbons with normal pentane, normal hexane, and isohexane providing most of the paraffinic components. Where multiple streams are combined to form a feedstock, the benzene in one of the feeds may be much higher than 25 wt.-%. The dilution effect of combining the streams results in the benzene being at a manageable level.

The isomerization zone and hydrogenation zone catalysts are often sulfur sensitive. Suitable guard beds or adsorptive separation processes may be used to reduce the sulfur concentration of the feedstock. The FIGURE shows the treatment of the feedstock to remove sulfur upstream of the feedstock drier, hydrogen addition point, and the hydrogenation zone. It is important that the sulfur guard bed be located upstream of the drier since water may be liberated from fresh guard bed adsorbent. The feed stream is heated by heat exchange with the effluent of the benzene saturation reactor using a heat exchanger before being passed to the sulfur guard bed. If needed, additional heat may be input into stream 10 before reaching sulfur guard bed 12. The feed stream may be heated with any suitable process stream such as the stabilizer bottoms or with a utility stream such as steam or hot oil.

Also, some of the possible isomerization zone catalysts suitable for use in this invention are highly sensitive to water and other contaminants. In order to keep water content within acceptable levels for such catalysts, the streams directed to the isomerization zone are first passed through at least one drier. The drier for this purpose reduces water content to 0.1 ppm or less, and suitable adsorption processes for this purpose are well known in the art. The specific placement of the driers in relation to the guard beds and other streams allows for low pressure driers to be used to dry the feedstream. Low pressure driers and their associated regeneration switching valves are much less costly than high pressure driers and are less costly to operate as well. As shown in the FIGURE, the feedstock passes through a drier and the hydrogen stream passes through another drier before the feedstock and the hydrogen stream are combined to form the combined feed. It is important to note that both the feedstock drier and the hydrogen drier are upstream of the hydrogenation zone.

This specific arrangement results in the elimination of the need for additional equipment such as a condenser, a receiver and a high pressure drier on the feedstock stream, and makes the most use of equipment commonly found in existing systems built at a time where there was less of a need to process benzene. Previous isomerization processes, where the benzene concentration in the feedstock was less than 5 wt.-%, often had a drier that operated at low pressure. In contrast, previous isomerization processes with higher concentrations of benzene in the feedstock, first saturated the benzene and then dried the product before passing the stream to the isomerization zone. Since the hydrogenated product stream was two-phase, a condenser and a receiver were required to provide a liquid stream that was sent to the driers. To avoid the loss of isopentanes in the receiver off-gas, the receiver and therefore the subsequent drier was operated at high pressure and a more costly high pressure drier was required. With the current need for existing processes to be revised to process feedstocks containing higher benzene concentrations, and the existing low pressure driers, a novel flow scheme was required to allow the processing of a benzene containing feedstock while at the same time only requiring a low pressure drier. In addition to the capital and operating cost savings associated with the elimination of the condenser and receiver and the ability to reuse existing low pressure feed driers, this flow scheme eliminates the need for sulfur guard beds on the hydrogen stream sent to the saturation reactor. All of the hydrogen used for the hydrogenation and isomerization zones is sent through hydrogen driers where both sulfur and water contained in the hydrogen stream are removed.

A hydrogen stream is combined with the feedstock to provide hydrogen for the hydrogenation and isomerization zones. When the hydrogen is added downstream of the feedstock treating section, the hydrogen stream also undergoes drying or other treatment, such as sulfur removal, necessary for the sustained operation of the isomerization zone or hydrogenation zone. The hydrogenation of benzene in the hydrogenation zone results in a net consumption of hydrogen. Although hydrogen is not consumed by the isomerization reaction, the isomerization of the light paraffins is usually carried out in the presence of hydrogen. Therefore, the amount of hydrogen added to the feedstock should be sufficient for both the requirements of the hydrogenation zone and the isomerization zone.

The amount of hydrogen admixed with the feedstock varies widely. For the isomerization zone alone, the amount of hydrogen can vary to produce anywhere from a 0.01 to a 10 hydrogen to hydrocarbon ratio in the isomerization zone effluent. Consumption of hydrogen in the hydrogenation zone increases the required amount of hydrogen admixed with the feedstock. The input through the hydrogenation zone usually requires a relatively high hydrogen to hydrocarbon ratio to provide the hydrogen that is consumed in the saturation reaction. Therefore, hydrogen will usually be mixed with the feedstock in an amount sufficient to create a combined feed having a hydrogen to hydrocarbon ratio of from 0.1 to 2. Lower hydrogen to hydrocarbon ratios in the combined feed are preferred to simplify the system and equipment associated with the addition of hydrogen. At minimum, the hydrogen to hydrocarbon ratio must supply the stoichiometric requirements for the hydrogenation zone. In order for the hydrogenation zone to operate at the mild conditions of this invention, it is preferable that an excess of hydrogen be provided with the combined feed. Although no net hydrogen is consumed in the isomerization reaction, the isomerization zone will have a net consumption of hydrogen often referred to as the stoichiometric hydrogen requirement which is associated with a number of side reactions that occur. These side reactions include saturation of olefins and aromatics, cracking and disproportionation. Due to the presence of the hydrogenation zone, little saturation of olefins and aromatics will occur in the isomerization zone. Nevertheless, hydrogen in excess of the stoichiometric amounts for the side reactions is maintained in the isomerization zone to provide good stability and conversion by compensating for variations in feedstream compositions that alter the stoichiometric hydrogen requirements and to prolong catalyst life by suppressing side reactions such as cracking and disproportionation. Side reactions left unchecked reduce conversion and lead to the formation of carbonaceous compounds, i.e., coke, that foul the catalyst. As a result, the effluent from the hydrogenation zone should contain enough hydrogen to satisfy the hydrogen requirements for the isomerization zone. In one embodiment the effluent from the hydrogenation zone has a hydrogen to hydrocarbon mole ratio of from about 0.05 to about 2, in another embodiment the ratio is about 0.1 to about 1.5 and in yet another embodiment the ratio is about 0.1 to 1.0.

It has been found to be advantageous to minimize the amount of hydrogen added to the feedstock. When the hydrogen to hydrocarbon ratio at the effluent of the isomerization zone exceeds about 0.20, it is not economically desirable to operate the isomerization process without the recovery and recycle of hydrogen to supply a portion of the hydrogen requirements. Facilities for the recovery of hydrogen from the effluent are needed to prevent the loss of product and feed components that can escape with the flashing of hydrogen from the isomerization zone effluent. These facilities add to the cost of the process and complicate the operation of the process. The isomerization zone can be operated with the effluent hydrogen to hydrocarbon ratio as low as 0.05 without adversely affecting conversion or catalyst stability. Accordingly where possible, the addition of hydrogen to the feedstock will be kept to below an amount that will produce a hydrogen to hydrocarbon ratio in excess of 0.20 in the effluent from the isomerization zone.

The combined feed in line 18 comprising hydrogen and the feedstock enter the hydrogenation zone. The hydrogenation zone is designed to saturate benzene at relatively mild conditions. The hydrogenation zone comprises a bed of catalyst for promoting the hydrogenation of benzene. Examples of catalyst compositions include platinum group, tin or cobalt and molybdenum metals on suitable refractory inorganic oxide supports such as alumina. In one embodiment, the alumina is an anhydrous gamma-alumina with a high degree of purity. The term platinum group metals refers to noble metals excluding silver and gold which are selected from the group consisting of platinum, palladium, germanium, ruthenium, rhodium, osmium, and iridium.

Such catalysts have been found to provide satisfactory benzene saturation at conditions including temperatures as low as 38° C. (100° F.), pressures from 1400 to 4800 kPa(g) (200 to 700 psig), an inlet hydrogen to hydrocarbon ratio in the range of 0.1 to 2, and a 1 to 40 liquid hourly space velocity (LHSV). Other suitable pressures include from about 2068 to about 4137 kPa(g) (300 to 600 psig) and from about 2413 to about 3792 kPa(g) (350 to 550 psig) and other suitable liquid hourly space velocities include from about 4 to about 20 and about 8 to about 20 $hr^{-1}$. In another embodiment of this invention, the feed entering the hydrogenation zone will be heated to a temperature in the range of 38 to 232° C. (100 to 450° F.), 127 to 232° C. (260 to 450° F.) or 149 to 204° C. (300 to 400° F.) by heat exchange with the effluent from the hydrogenation and isomerization zones. The exothermic saturation reaction increases the heat of the combined feed and saturates essentially all of the benzene contained therein. The effluent from the hydrogenation zone provides a saturated feed for the isomerization zone that will typically contain from 0.01 wt.-% to 5 wt.-% or from 0.1 wt.-% to 1.5 wt.-% benzene or from 0.1 to 1.0 wt.-% benzene.

With the hydrogenation reaction being exothermic, the saturated feed from the hydrogenation reactor is typically at a temperature in the range of 149 to 288° C. (200 to 550° F.); 177 to 274° C. (350 to 525° F.); or 204 to 274° C. (400 to 525° F.). The isomerization zone operates at a lower temperature range, so the heat of the saturated feed may be recovered and used to provide heat to other colder streams either within the process or from outside the process. For example, the saturated feed may be heat exchanged with the combined feed and with the feedstock. If the saturated feed is still too high in temperature even after heat exchange, the saturated feed may be cooled using conventional techniques.

Saturated feed from the hydrogenation zone enters the isomerization zone for the rearrangement of the paraffins contained therein from less highly branched hydrocarbons to more highly branched hydrocarbons. Furthermore, if there are any unsaturated compounds that enter the isomerization zone after passage through the hydrogenation zone, these residual amounts of unsaturated hydrocarbons will be quickly saturated in the isomerization zone. The isomerization zone uses a solid isomerization catalyst to promote the isomerization reaction. There are a number of different isomerization catalysts that can be used for this purpose. The zeolitic type isomerization catalysts are well known and are described in detail in U.S. Pat. Nos. 3,442,794 and 3,836,597. Other catalysts include those such as described in U.S. Pat. No. 6,927,188.

The high chloride catalyst on an alumina base that contains platinum is also well known in the art and not described in detail here. This type of catalyst also contains a chloride component. The chloride component termed in the art "a combined chloride" is present in an amount from about 2 to about 10 wt.-% based upon the dry support material.

It is generally known that high chlorided platinum-alumina catalysts of this type are highly sensitive to sulfur and oxygen-containing compounds. Therefore, the feedstock must be relatively free of such compounds. A sulfur concentration no greater than 0.1 ppm is generally required at the reactor inlet. The presence of sulfur in the feedstock serves to temporarily deactivate the catalyst by platinum poisoning. Activity of the catalyst may be restored by hot hydrogen stripping of sulfur from the catalyst composite or by lowering the sulfur concentration in the reactor feed to below 0.1 ppm so that the hydrocarbon will desorb the sulfur that has been absorbed on the catalyst. Water can act to permanently deactivate the catalyst by removing high chloride from the catalyst and replacing it with inactive aluminum hydroxide. Therefore, water, as well as oxygenates, in particular $C_1$-$C_5$ oxygenates, that can decompose to form water, can only be tolerated in very low concentrations. In general, this requires a limitation of oxygenates in the feed to about 0.1 ppm or less. As previously mentioned, the feedstock may be treated by any method that will remove water and sulfur compounds. Sulfur may be removed from the feedstock by hydrotreating. Adsorption processes for the removal of sulfur and water from hydrocarbon streams are also well known to those skilled in the art.

Operating conditions within the isomerization zone are selected to maximize the production of isoalkane product from the feed components. Inlet temperatures to, and temperatures within the reaction zone will usually range from about 38° C. to about 260° C. (100° F. to 500° F.) or 104° C. to 204° C. (220° F. to 400° F.) or 104° C. to 177° C. (220° F. to 350° F.). Lower reaction temperatures are preferred for purposes of isomerization conversion since they favor isoalkanes over normal alkanes in equilibrium mixtures. The isoalkane product recovery can be increased by opening some of the cyclohexane rings produced by the saturation of the benzene. However, if it is desired, maximizing ring opening usually requires temperatures in excess of those that are most favorable from an equilibrium standpoint. For example, when the feed mixture is primarily $C_5$ and $C_6$ alkanes, temperatures in the range of 60° to 160° C. are desired from a normal-isoalkane equilibrium standpoint but, in order to achieve significant opening of $C_5$ and $C_6$ cyclic hydrocarbon ring, the preferred temperature range for this invention lies between 100° to 200° C. When it is desired to also isomerize significant amounts of $C_4$ hydrocarbons, higher reaction temperatures are required to maintain catalyst activity. Thus, when the feed mixture contains significant portions of $C_4$-$C_6$ alkanes the most suitable operating temperatures for ring opening and isoalkane equilibrium coincide and are in the range from 145° to 225° C. The reaction zone may be maintained over a wide range of pressures. Pressure conditions in the isomerization of $C_4$-$C_6$ paraffins range from 1380 kPa(g) to 4830 kPa(g) (200 to 700 psig). Higher pressures favor ring opening, therefore, embodiments may use pressures for this process in the range of from 2410 kPa(g) to 4830 kPa(g) (350 to 700 psig) when ring opening is desired. The feed rate to the reaction zone can also vary over a wide range. These conditions include liquid hourly space velocities ranging from 0.5 to 12 $hr^{-1}$, or between 0.5 and 3 $hr^{-1}$.

Depending upon the catalyst selected, operation of the reaction zone may also require the presence of a small amount of an organic chloride promoter. The organic chloride promoter serves to maintain a high level of active chloride on the catalyst as small amounts of chloride are continuously stripped off the catalyst by the hydrocarbon feed. The concentration of promoter in the reaction zone is usually maintained at from 30 to 300 ppm. Suitable promoter compounds include oxygen-free decomposable organic chlorides such as perchloroethylene, carbon tetrachloride, proplydichloride, butylchloride, and chloroform to name only a few of such compounds. The addition of chloride promoter after the hydrogenation reactor, as shown in the FIGURE, may be carried out at such a location to expose the promoter to the highest available temperature and assure its complete decomposition. The need to keep the reactants dry is reinforced by the presence of the organic chloride compound which may convert, in part, to hydrogen chloride. As long as the process streams are kept dry, there will be no adverse effect from the presence of small amounts of hydrogen chloride.

A preferred manner of operating the process is in a two-reactor, reaction zone system. The catalyst used in the process can be distributed equally or in varying proportions between the two reactors. The use of two reaction zones permits a variation in the operating conditions between the two reaction zones to enhance isoalkane production. The two reaction zones can also be used to perform cyclic hydrocarbon conversion in one reaction zone and normal paraffin isomerization in the other. In this manner, the first reaction zone can operate at higher temperature and pressure conditions that favor ring opening but performs only a portion of the normal to isoparaffin conversion. The two stage heating of the combined feed, e.g., as provided by exchangers 26 and 24, facilitates the use of higher temperatures therein in a first isomerization reactor. Once cyclic hydrocarbon rings have been opened by initial contact with the catalyst, the final reactor stage may operate at temperature conditions that are more favorable for isoalkane equilibrium.

Another benefit of using two reactors is that it allows partial replacement of the catalyst system without taking the isomerization unit off stream. For short periods of time, during which the replacement of catalyst may be necessary, the entire flow of reactants may be processed through only one reaction vessel while catalyst is replaced in the other.

Whether operated with one or two reaction zones, the effluent of the process will enter separation facilities for the recovery of an isoalkane product. At minimum, the separation facilities divide the reaction zone effluent into a product stream comprising $C_5$ and heavier hydrocarbons and a gas stream which is made up of $C_3$ lighter hydrocarbons and hydrogen. To the extent that $C_4$ hydrocarbons are present, the acceptability of these hydrocarbons in the product stream will depend on the blending characteristics of the desired product, in particular vapor pressure considerations. Consequently, $C_4$ hydrocarbons may be recovered with the heavier isomerization products or withdrawn as part of the overhead or in an independent product stream. Suitable designs for rectification columns and separator vessels to separate the isomerization zone effluent are well known to those skilled in the art.

When hydrogen is received for recycle from the isomerization zone effluent, the separation facilities, in simplified form, can consist of a product separator and a stabilizer. The product separator operates as a simple flash separator that produces a vapor stream rich in hydrogen with the remainder of its volume principally comprising $C_1$ and $C_2$ hydrocarbons. The vapor stream serves primarily as a source of recycle hydrogen which is usually returned directly to the hydrogenation process. The separator may contain packing or other liquid vapor separation devices to limit the carryover of hydrocarbons. The presence of $C_1$ and $C_2$ hydrocarbons in the vapor stream do not interfere with the isomerization process, therefore, some additional mass flow for these components is accepted in exchange for a simplified column design. The remainder of the isomerization effluent leaves the separator as a liquid which is passed on to a stabilizer, typically a trayed column containing approximately 30 trays. The column will ordinarily contain condensing and reboiler loops for the withdrawal of a light gas stream comprising at least a majority of the remaining $C_3$ hydrocarbons from the feed stream and a light bottoms stream comprising $C_5$ and heavier hydrocarbons. Normally when the isomerization zone contains only a small quantity of $C_4$ hydrocarbons, the $C_4$'s are withdrawn with the light gas stream. After caustic treatment for the removal of chloride compounds, the light gas stream will ordinarily serve as fuel gas. The stabilizer overhead liquid, which represents the remainder of the isomerization zone effluent passes back to the fractionation zone as recycle input.

A simplified flow scheme for use without hydrogen recycle stream was described in the FIGURE. In the arrangement of the FIGURE, all of the excess hydrogen from the isomerization zone is taken with the overhead stream from the stabilizer drum or receiver. Since, as a precondition for use of this arrangement, the amount of hydrogen entering the stabilizer is low, the rejection of hydrogen with the fuel gas stream does not significantly increase the loss of product hydrocarbons.

In order to more fully illustrate the process, the following theoretical example is presented to demonstrate the operation of the process utilizing the flow scheme of the FIGURE. All of the numbers identifying vessels and lines correspond to those given in the FIGURE. The Table provides illustrative compositions of streams of the process. The Table is merely an example, and stream compositions may vary from those shown.

A $C_5$ plus naphtha fresh feed having a composition shown in the Table enters through line 10 and is heat exchanged with the hydrogenation zone effluent before being passed through sulfur guard bed 12 to remove sulfur components. The sulfur-free feed is conducted in line 13 to low pressure drier 11 to remove water. Feed in line 13 may be combined with recycle normal alkanes in line 64 from deisohexanizer 58 prior to being dried in low pressure drier 11. Furthermore, if some or all of the feed is light reformate, it is expected that the light reformate will already be sulfur-free and sulfur guard bed 12 may be bypassed or eliminated. Optional line 70, shown as a dashed line, shows light reformate feed bypassing sulfur guard bed 12. Reducing the amount of material passing through the sulfur guard bed may result in a smaller guard bed being required thus reducing costs. Hydrogen in line 14 is dried in drier 16 and combined with dried feed in line 15 to form a combined feed.

Combined feed 18 is passed through a series of heat exchangers such as exchangers 24, 25 and 26 to heat the feed to a temperature of 149° C. to 204° C. (300° to 400° F.) which then enters the hydrogenation reactor at a pressure of 3450 kPa(g) (500 psig). In the hydrogenation reactor, the combined feed is contacted with a catalyst comprising a platinum metal on a chlorided platinum alumina support at an LHSV of 20. Contact of the combined feed with the hydrogenation catalyst produces a saturated feed that is withdrawn by line 34 and has no more than about 0.5 wt.-% benzene. The hydrogenation zone heats the saturated feed to a temperature of 177 to 274° C. (350° to 525° F.). Since the temperature required for the isomerization zone is less than the temperature of the saturated feed, the saturated feed is heat exchanged with the combined feed in line 18 and with the fresh feed in line 10. If necessary, the saturated feed may also be cooled. The saturated feed in line 34 is passed on to the isomerization zone at a pressure of 3240 kPa(g) (470 psig). Perchloroethylene is added to the saturated feedstream at a rate of 150 wt. ppm which then enters the reactor train 30 and 22 of the isomerization zone. In the isomerization zone, the saturated feed stream contacts an alumina catalyst such as one having 0.25 wt.-% platinum and 5.5 wt.-% chloride. The converted isomerization zone feed passed out of the reactor train in line 20 at a temperature of 93 to 204° C. (200 to 400° F.) and a pressure of 3100 kPa(g) (450 psig) and has an exemplary composition as shown in the Table.

After heat exchange with combined feed 18, cooled isomerization zone effluent in line 36 enters the stabilizer column 38 for the recovery of the product and removal of light gases. Column 38 has, for example, 30 trays and the feed may enter above tray 15. Column 38 splits the isomerization zone effluent into an overhead 42 which is cooled and condensed 44 to provide a recycle 46 and a fuel gas stream 50. Because of the chloride in the stream, the fuel gas stream 50 is passed through scrubber 52 to remove any chloride and provide a scrubbed fuel gas stream 56. Spent caustic is removed from scrubber 52 in stream 54. An isomerization zone product 40 is withdrawn from the bottom of stabilizer column 38 and has the exemplary composition shown in the Table. Isomerization zone product 40 is passed to deisohexanizer 58 to separate low octane normal and monomethyl alkanes into stream 64 which may be recycled to combine with the feed stock in line 13. The pentanes, dimethyl-butanes, and some monomethyl alkanes removed in DIH overhead 60 are combined with the C6 naphthenes and C7+ in DIH bottoms 62 to form the process product stream 66.

This example demonstrates the ability of the process to saturate benzene using a flow scheme that allows low pressure feedstock driers and requires no condensing of the feed that would also require a receiver with hydrogen venting and additional pumps. The combined feed is heat exchanged with the effluents of the isomerization reactors and the benzene saturation reactor, and the benzene saturation effluent is also heat exchanged with the fresh feed. All values in the table are merely exemplary of one embodiment, and the compositions of the stream may vary with different applications.

TABLE

Stream Compositions in kmol/hr

| | Stream Number | | | | | |
|---|---|---|---|---|---|---|
| | 10 | 14 | 34 | 20 | 56 | 40 |
| Hydrogen | 0.0 | 46.0 | 14.4 | 5.0 | 5.0 | 0.0 |
| C1-C4 | 0.1 | 0.1 | 0.2 | 3.7 | 3.6 | 0.1 |
| Isopentane | 10.4 | 0.0 | 10.4 | 20.8 | 0.2 | 20.6 |
| Normal Pentane | 15.6 | 0.0 | 15.6 | 7.1 | 0.0 | 7.1 |
| Cyclopentane | 1.7 | 0.0 | 1.7 | 1.4 | 0.0 | 1.4 |
| Dimethylbutanes | 4.5 | 0 | 4.5 | 20.0 | 0 | 20.0 |
| Methylpentanes | 21.4 | 0 | 21.4 | 24.1 | 0 | 24.1 |
| Normal Hexane | 19.9 | 0.0 | 19.9 | 6.2 | 0.0 | 6.2 |
| Methylcyclopentane | 7.9 | 0.0 | 7.9 | 7.1 | 0.0 | 7.1 |
| Cyclohexane | 5.9 | 0.0 | 16.4 | 8.3 | 0.0 | 8.3 |
| Benzene | 10.7 | 0.0 | 0.2 | 0.0 | 0.0 | 0.0 |
| C7+ | 1.9 | 0 | 1.9 | 3.2 | 0 | 3.2 |
| Total | 100 | 46.1 | 114.5 | 106.9 | 8.8 | 98.1 |

The invention claimed is:

1. A process for the hydrogenation and decyclization of benzene and the isomerization of $C_5$-$C_6$ paraffins with a feedstock comprising $C_5$-$C_6$ paraffins and at least 1 wt.-% benzene, said process comprising:
    (a) passing the feedstock, without venting hydrogen or condensing, to a drier, to remove water and thereby dry the feedstock and generate a dried feedstock comprising less than 0.5 wt.-% water;
    (b) combining the dried feedstock with a hydrogen-rich gas stream to produce a combined feed;
    (c) passing the combined feed, at a temperature of from about 38 to about 232° C. (about 100 to about 450° F.), to a hydrogenation zone and contacting said combined feed with a hydrogenation catalyst at hydrogenation conditions to saturate benzene and generate a hydrogenation zone effluent having a temperature in the range of about 149 to about 288° C. (300 to 550° F.) and comprising less than 1.5 wt. % benzene;
    (d) adjusting the temperature of the hydrogenation zone effluent to a range of about 104 to about 204° C. (220 to 400° F.) by at least heat exchanging the hydrogenation zone effluent with the combined feed;
    (e) passing at least a portion of the hydrogenation zone effluent to an isomerization zone and contacting with an isomerization catalyst at isomerization and decyclization conditions to isomerize $C_5$-$C_6$ paraffins and decyclize benzene;
    (f) recovering an isomerate product from the isomerization zone;
    (g) separating the isomerate product to remove $C_4$ and lighter hydrocarbons and generate a stabilizer bottoms stream; and
    (h) recovering the stabilizer bottoms stream as product.

2. The process of claim 1 further comprising passing at least a portion of the feedstock through a sulfur guard bed to remove sulfur-containing components prior to passing the feedstock to the drier.

3. The process of claim 2 further comprising combining a second feed with the feedstock after passing the feedstock through the sulfur guard bed and prior to passing to the drier.

4. The process of claim 1 wherein the feedstock comprises about 1 to about 25 wt.-% benzene.

5. The process of claim 1 wherein the combined feed to the hydrogenation zone is heated to about 127 to 232° C. (260 to 450° F.).

6. The process of claim 1 wherein the hydrogenation zone effluent has from about 0.01 to about 1.5 wt.-% benzene.

7. The process of claim 1 wherein the hydrogenation zone effluent has a temperature in the range of about 177 to 274° C. (350 to 525° F.).

8. The process of claim 1 wherein the hydrogenation zone effluent is adjusted to a temperature in the range of about 38 to 260° C. (100 to 500° F.).

9. The process of claim 1 wherein the hydrogen-rich gas stream is mixed with said feedstock to produce a hydrogen to hydrocarbon ratio in the range of 0.1 to 2 in the combined feed.

10. The process of claim 1 wherein said feedstock additionally comprises $C_4$ paraffins.

11. The process of claim 1 wherein the hydrogenation conditions include a pressure of from 1380 to 4830 kPa(g) (200 to 700 psig), a liquid hourly space velocity of from 1 to 40 and a hydrogen to hydrocarbon ratio of from 0.1 to 2.

12. The process of claim 1 wherein said isomerization catalyst comprises a chlorided platinum catalyst on alumina support.

13. The process of claim 1 wherein a chloride concentration of from 30-300 ppm is maintained in the isomerization zone by injecting a chloride compound into the hydrogenation zone effluent.

14. The process of claim 1 wherein the isomerization zone includes at least two reactors in series, the first reactor is operated at conditions to open saturated hydrocarbon rings, said conditions including a temperature in excess of 143° C. (290° F.) and a pressure of at least 1380 to 4690 kPa(g) (200 to 680 psig) and the second reactor in the series is operated at conditions to increase the concentration of $C_5$-$C_6$ isoalkanes including a temperature in the range of 38 to 177° C. (104 to 350° F.).

15. The process of claim 1 wherein the drier of step 1(a) is a low pressure drier.

16. The process of claim 1 wherein the hydrogenation catalyst comprises a platinum group metal component on a solid support.

* * * * *